United States Patent [19]
Mönch

[11] Patent Number: 5,840,261
[45] Date of Patent: Nov. 24, 1998

[54] CONTAINER FOR MEDICAL INSTRUMENTS

[75] Inventor: Harry Mönch, Knittlingen, Germany

[73] Assignee: Richard Wolf GmbH, Knittlingen, Germany

[21] Appl. No.: 552,607

[22] Filed: Nov. 3, 1995

[30] Foreign Application Priority Data

Nov. 12, 1994 [DE] Germany ............ 44 40 514.6

[51] Int. Cl.⁶ ............................. A61L 2/06
[52] U.S. Cl. ............ 422/300; 134/135; 422/297
[58] Field of Search ............... 422/300, 297; 134/135, 166 R, 201

[56] References Cited

U.S. PATENT DOCUMENTS

| | | | |
|---|---|---|---|
| 4,748,993 | 6/1988 | Llewellyn | 134/166 R |
| 4,830,200 | 5/1989 | Zambano et al. | 211/181 |
| 4,865,821 | 9/1989 | Langdon | 422/300 |
| 4,899,885 | 2/1990 | Van Koert | 206/512 |
| 5,433,929 | 7/1995 | Riihimaki et al. | 422/297 |
| 5,433,930 | 7/1995 | Taschner | 422/300 |
| 5,505,916 | 4/1996 | Berry, Jr. | 422/300 |

FOREIGN PATENT DOCUMENTS 8525574  12/1985  Germany .

OTHER PUBLICATIONS

Telescope–Sterilisation–Basket brochure by Riwoplan Clinica, Germany. Apr. 26, 1991.

Primary Examiner—Krisanne Thornton
Attorney, Agent, or Firm—Cohen, Pontani, Lieberman & Pavane

[57] ABSTRACT

A container for medical instruments or instrument parts constructed from wire formed parts. The container has a lower part and a lid with a handle for use in removing the lid from the lower part. Supports are removable and adjustably positioned within and define open topped receptacles for retaining the instruments within the lower part, the instruments are fixed in their position by braces when the container is closed. The lid in its closed position is connected to the lower part on one side by a positive locking mechanism, and on its opposite side by a latching mechanism. After releasing the latching mechanism the positive locking mechanism can be released by raising or tilting the lid. The handle is made from wire-formed parts and is positioned in the upper plane of the lid.

13 Claims, 5 Drawing Sheets

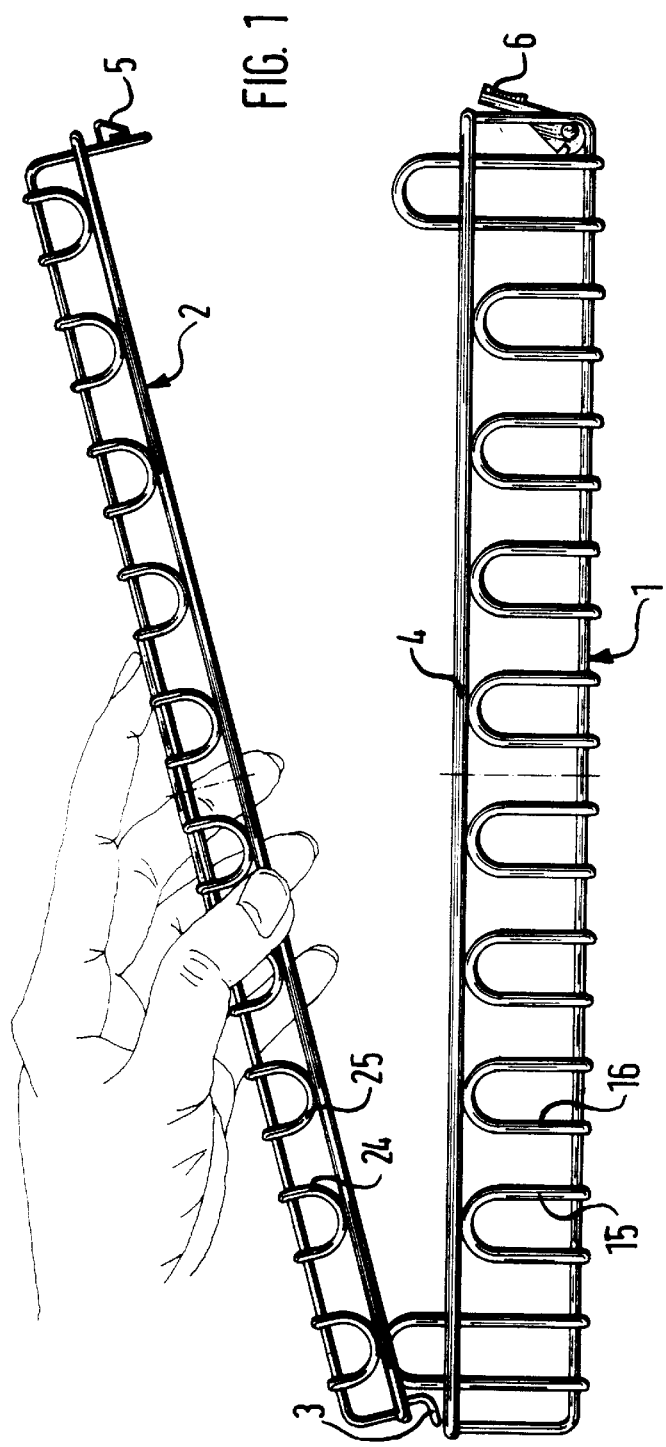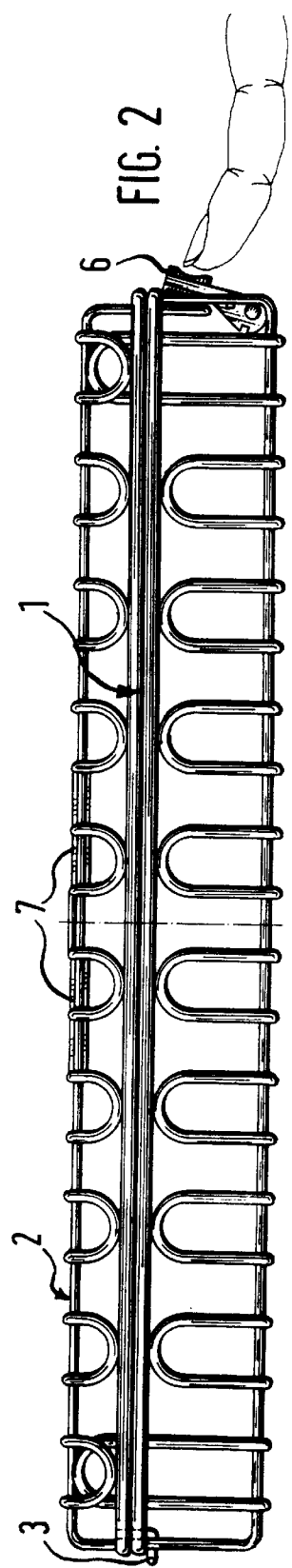

CONTAINER FOR MEDICAL INSTRUMENTS

BACKGROUND OF THE INVENTION

1. Field of the Invention

The invention relates to a container for medical instruments in particular the container is endoscopes and endoscope optics, structured essentially as a cuboid wire construction from wire-formed parts, the container has a lower part and, a lid which is removable from the lower part. Supports open topped receptacles are arranged and fixed inside the lower part for placement of instruments in the lower part, the instruments are fixed in their position with braces when the container is closed.

2. Brief Description of the Prior Art

Such containers are well known. For example, German Patent Application DEA-39 18 147 discloses a container in which; instruments or instrument parts to be rinsed, sterilized or disinfected are accomodated dated. The container has a wide-meshed wire construction ensuring that fluids or gases for the above mentioned purposes can be introduced into the container and evenly distributed around the instruments to be treated.

Moreover such wire basket type containers can serve to store and transport instruments, for example, instruments having been subjected to the above mentioned sterilization treatment, remain preserved in the container and are kept sterile by closedly packing the container together with the instruments in a tubular foil.

Containers of this type are well known but require for improvement with regard to their handling of instruments and design. In particular, in comparison with previous solutions, from a design and handling point of view, a simpler connection of both the lid and supports to the lower part is needed. Construction of the container so that no parts protrude on the outside of the container to prevent the stacking of several containers or could damaging the packaging covering the container is also desirable.

SUMMARY OF THE INVENTION

In accordance with the invention, this object is achieved by designing a container such that the lid, in its closed position is connected on one side to the lower part by a positive locking mechanism and on its opposite side by a latching mechanism, that after releasing the latching, the positive locking mechanism can be undone by tilting the lid. A handle made from wire-formed parts is positioned in an upper plane of the lid for use in tilting the lid and the supports are removably attached to the lower part.

The lid appropriately grips a horizontal circumferential carrier of the lower part on one side through projections extending therefrom and is latched with this carrier on the opposite side with a spring element which is adjustable on the outside by way of a key for releasing the latching.

With a container designed in such a manner, the lid can be connected to the lower part simply, by applying only one hand and with a pressure to the lid, it can be unproblematically latched to the lower part, without having to undertake any particular manipulation. Conversely, after undoing the latching, the lid can, by tilting, be brought into a position inclined towards the lower part and lifted off the lower part by releasing the positive locking. The removal of the lid from the lower part is thus made easier when the lid is restrained and resiliently connected to the lower part and in a manner such that the container already partly opens automatically by tilting the lid after releasing the latching.

The handle to be provided on the lid may advantageously be formed from two U-shaped wire-formed parts, their apexes lying opposite each other. Since these handle parts are situated in the upper plane of the lid, they do not protrude towards the outside and therefore present no handicap to the stacking of the containers.

The supports are positioned to run cross-wise through the interior space of the lower part and at both their respective ends may be detachably and adjustably connected to the lower part.

An advantageous solution for the attachment of the supports consists of restraining the supports, which are made from wire-formed parts, between two side walls of the lower part. Projections at each of the two ends of the supports are gripped in the space between two webs of the lower part and lie internally with shoulders positioned against these webs. In an similar manner, the braces may also be so designed and connected to the webs of the side walls of the lid.

Furthermore each receptacle, made from wire-formed supports may comprise respectively of two parallel, essentially U-shaped open-topped bends for receiving the instruments, whilst the instruments placed in the receptacles in the closed container are fixed in their position by the webs of the braces.

A further advantageous possibility for the design of the supports and their attachment to the lower part comprises in forming the supports from a plastic mould including at least one recess for receiving the instrument and subsequently providing, in the upper region of each recess, two flaps which when not loaded, clear the opening of the receptacle and when loaded are elastically swung by the lid into a position in which the flaps, close the receptacle.

Both flaps associated with each receptacle can run convergingly upwards in the empty or unloaded condition, the free ends of the flaps opposing each other at a certain distance, such that the placing of the instruments into the receptacles without any effort is made possible.

For the purpose of fixing these supports to the lower part, each is inserted into a holder positioned on the base of the lower part, the holder includes resiliently swinging clamps for fixing the supports, for example with the clamping force of one of the clamps applied to the support. It is also possible to fix the supports to the holder using a positive locking arrangement with the clamps. For this purpose hooks may be provided on the clamps which grip recesses on the supports and prevent these supports from lifting from the holders.

BRIEF DESCRIPTION OF THE DRAWINGS

The invention is hereinafter described in more detail by embodiments of the invention represented in the drawings. The drawings in which like numerals denote identical elements show:

FIG. 1 is a side view of a container with the lid removed from the lower part, without the supports or braces, FIG. 2 is a side view of the container according to FIG. 1, with the lid placed on the lower part.

DETAILED DESCRIPTION OF THE PREFERRED EMBODIMENTS

Figure 4:
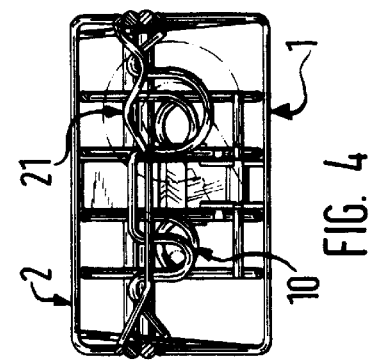
FIG. 4 is a sectional view taken along the line IV—IV in FIG. 3.

The oblong and essentially cuboid container comprises a lower part 1 and a lid 2, which are constructed from wire-formed parts in a manner already known per se (c.f. DE-A-3918147).

The lid as represented in the drawings comprises, on its left front side, which, from the tilted position of the lid (FIG. 1), by laterally moving the lid, move under a horizontal circumferential carrier 4 of the lower part 1 and by swinging the lid 2 into the closed position (FIG. 2) grip under the carrier 4 to hook the lid 2 to the lower part 1 and thereby connect the lid 2 and the lower part 1 on this side by a positive locking engagement. On the opposite side, the lid 2 is automatically latched to the lower part 1.

Figure 6:
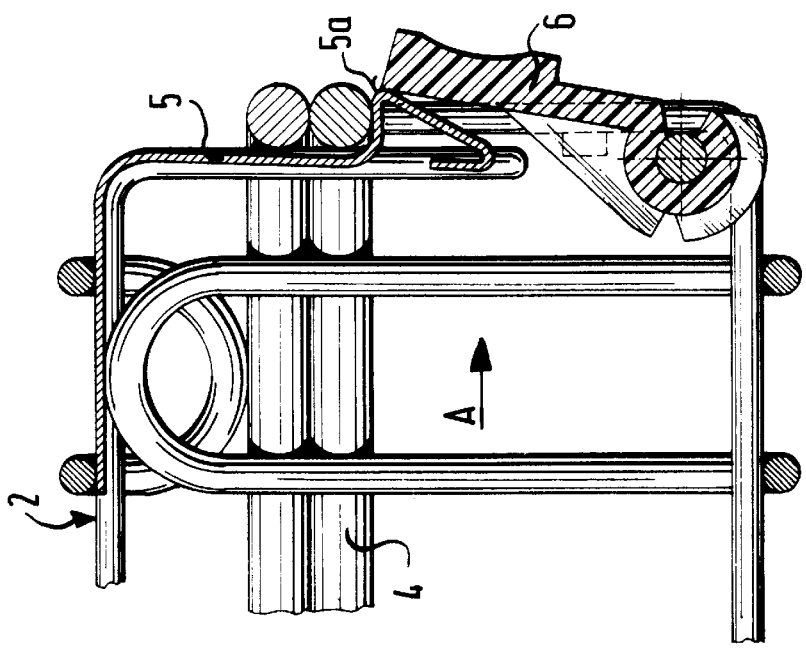
FIG. 6 is a partial cross sectional view taken through the latching mechanism of the container of FIG. 3.

To automatically latch the lid 2 to the lower part 1, the lid 2 comprises a spring element 5 which, snaps under and partly behind the carrier 4 with a nose 5a when moved in the closing position. By operating a key 6, which is swivelly mounted and spring loaded on the lower part 1, in a direction towards the spring element 5, counterclockwise as illustrated in FIG. 6, the key pushes against the nose 5a for releasing the latch, adjusting the spring element 5 towards the inside of the carrier so far that the nose 5a is released from the carrier 4 and the lid 2 when gripped by the hand of a user on the handle 7 is tilted about the positive locking engagement formed by projections 3 and carrier 4 and can then be completely lifted from the lower part 1 (FIG. 1).

Figure 5:
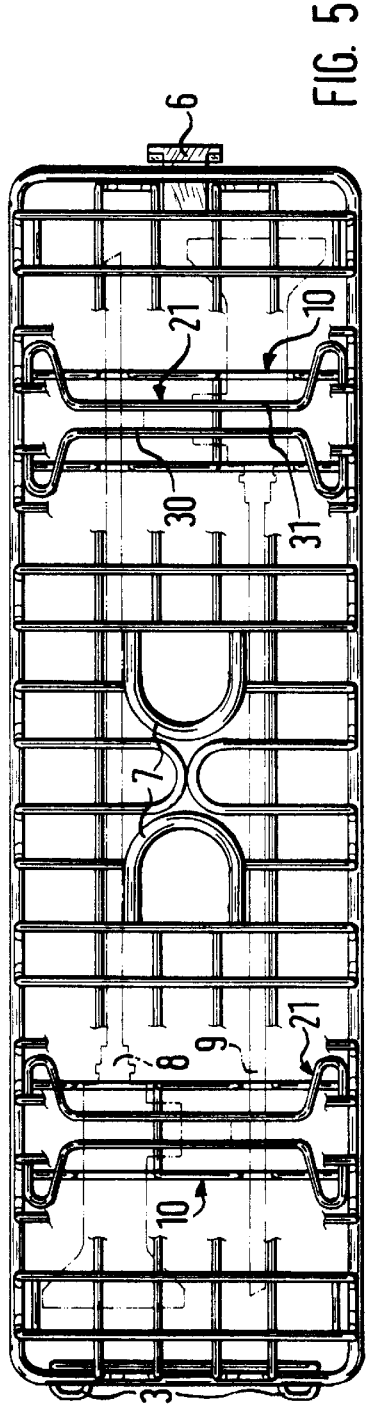
FIG. 5 is a top plan view of the embodiment shown in FIG. 3.
Figure 7:
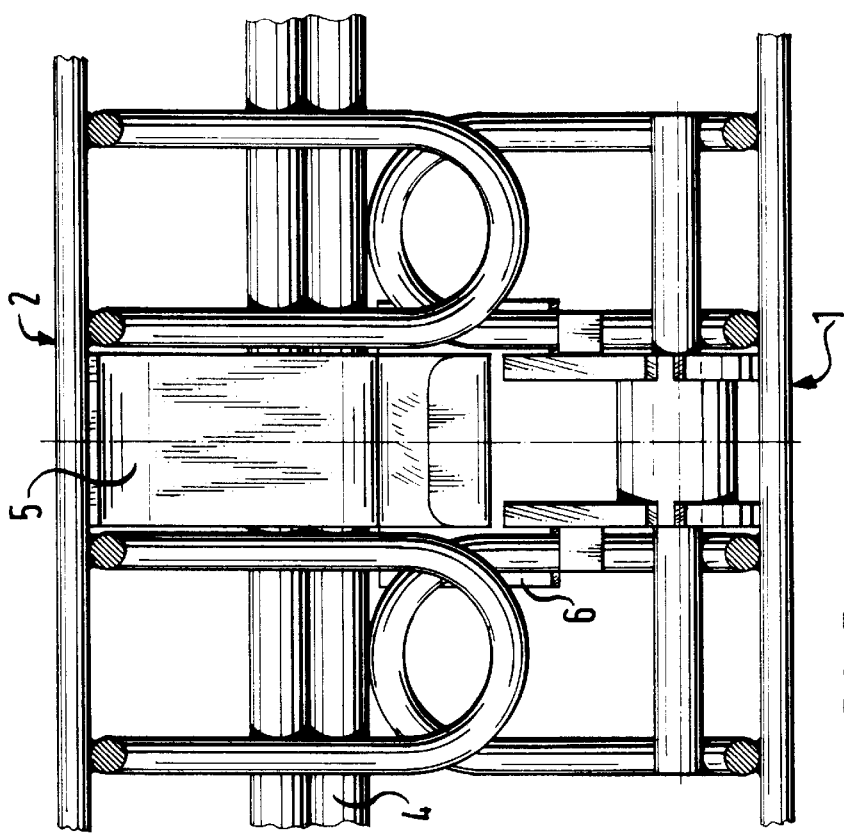
FIG. 7 is a partial cross sectional view taken in the direction of arrow A of the embodiment shown in FIG. 6.

The handle 7 provided in the upper plane of the lid 2 has two U-shaped wire-formed parts, which with their apex and arcs lie opposite each other as shown in FIG. 5, such that they can be comfortably gripped with two fingers of a hand.

Figure 3:
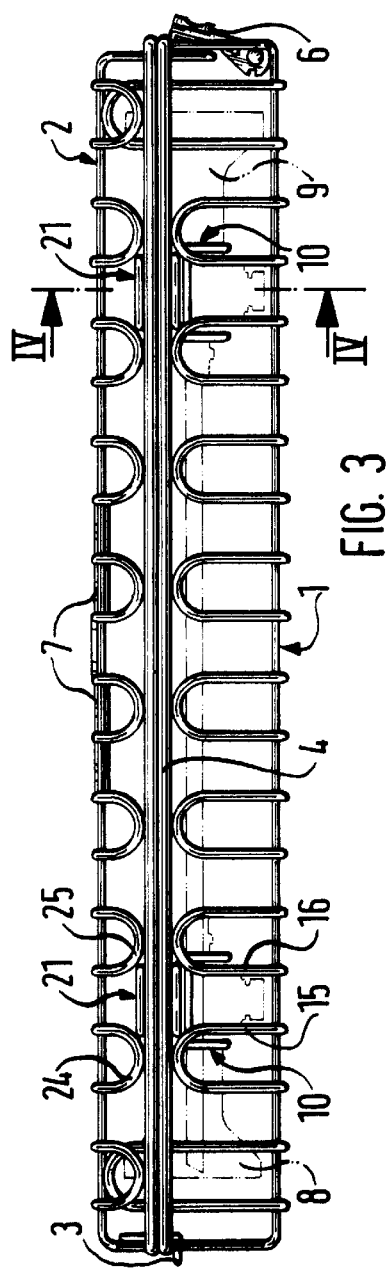
FIG. 3 is a side view of the container corresponding to FIG. 2 with supports, braces and endoscope optics situated therein.

The container may be constructed as shown in FIGS. 3 to 5, such that it may receive two endoscope optics 8, 9 illustrated by the dot-dashed lines. In this case the supports 10 which are to be attached to the lower part 1 at an appropriate distance from one another, each comprise two open receptacles in which the optics may be placed from above when the lid 2 is removed. Otherwise the supports 10, described in more detail later run cross-wise through the interior space of the lower part 1 and at both their ends may be detachably connected to said lower part 1.

Figure 8:
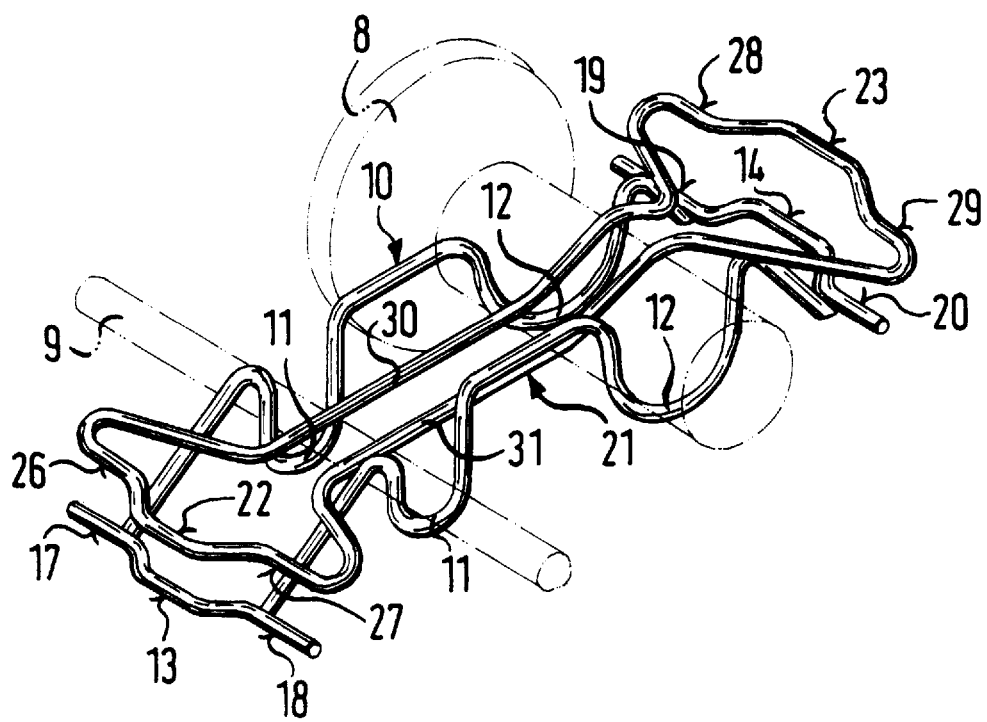
FIG. 8 is a support and brace cooperating as wire-formed parts.

With the support 10 shown in FIG. 8, also made from wire-formed parts, the receptacles 11, 12 for the optics 8,9 are each formed from two parallel essentially U-shaped and open-topped arches. At both ends, each of the supports 10 comprise a projection 13, 14 with which they grip inside the space between two vertical webs 15, 16 of the lower part 1 and with shoulders 17,18 and 19,20 respectively internally lying restrained against these webs 15,16.

In a similar manner, the braces 21 which are also formed from wire are restrained and attached between the two longitudinally arranged side walls of the lid 2, each of the braces 21 being provided at their ends with a projection 22, 23 which are gripped within a space between two vertical webs 24, 25 of the lid 2 and which support themselves internally against these webs with projections 26, 27 and 28, 29.

Moreover, according to FIG. 8, the braces 21 have parallel webs 30, 31 which, when the container is closed, pass straight across the receptacles 11, 12 and prevent the optics 8, 9 from falling from the container during any mishandling. Furthermore the webs 30, 31 may directly contact the optics 8,9, in order to better fix them in position. In such cases it is particularly useful to coat the supports and braces with resilient plastic, in order to prevent any damage to the optics 8,9.

Figure 9:
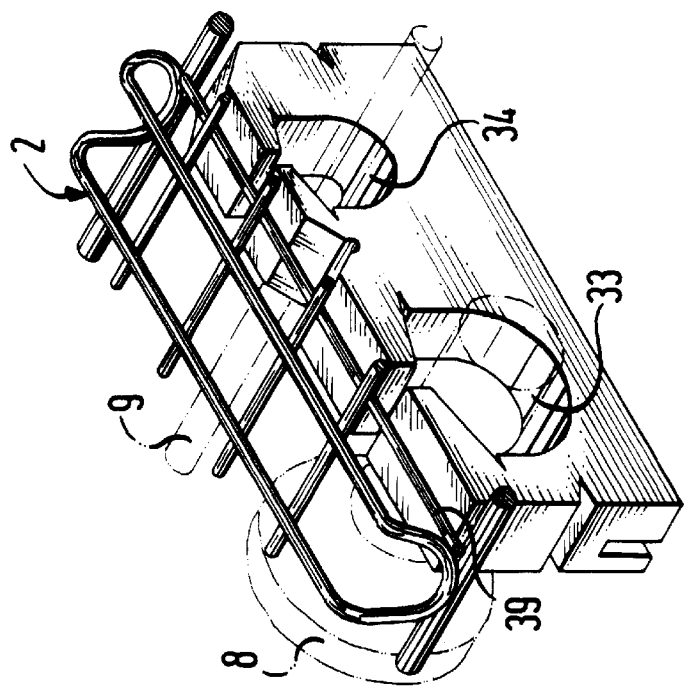
FIG. 9 is a perspective view of a second embodiment of the support and its attachment to the lower part.
Figure 10:
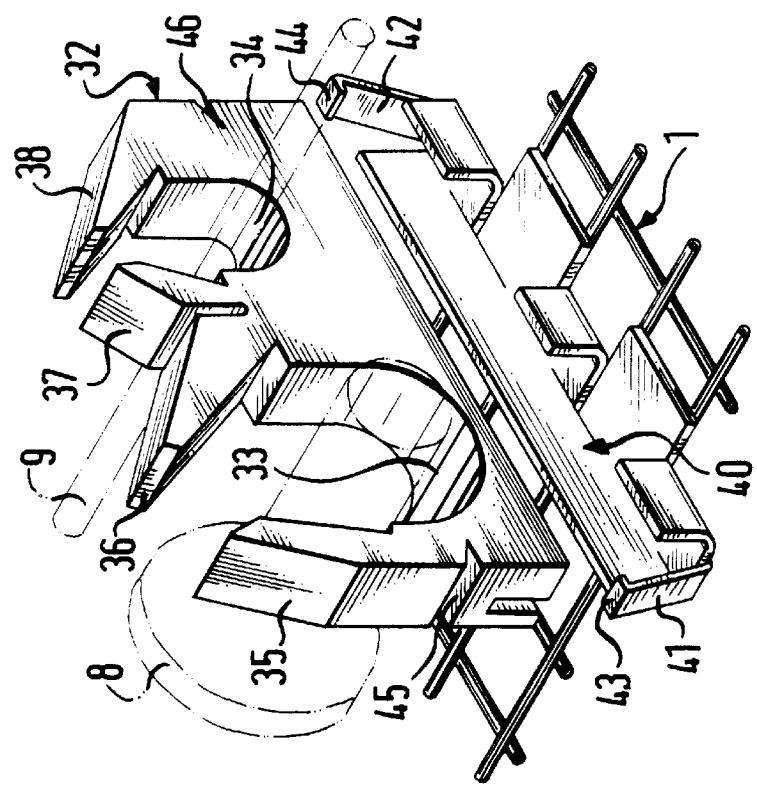
FIG. 10 is a perspective view of the second embodiment of the support and the lid.

The support 32 shown in FIGS. 9 and 10 is, as with the previously described support, to be attached to the lower part 1 at least in duplicate, and consists of a block-shaped moulding made from resilient plastic, in particular silicon plastic or similar material. In this embodiment, the support comprises two receptacles 33, 34, for receiving instruments to be rinsed such as the previously mentioned optics 8,9.

At the upper part of each of the two receptacles 33 and 34, the support 32 is provided with two flexible flaps 35, 36 and 37, 38 which in the unloaded condition as shown in FIG. 9 run convergingly upwards, the free ends of the flaps of each receptacle opposing each other at a certain distance, provided free access for receiving the instruments which are to be placed into said receptacles 33,34.

If on the other hand, when the flaps are subjected to a downwards force, for example by a transverse web 39 provided on the lid 2, on closing the lid 2, the flaps are twisted into the position shown in FIG. 10, in which they close the receptacles 33, 34 at the top and serve as rests for the optics 8,9.

Each of the supports 32 are inserted into a holder 40 mounted on the bottom of the lower part, the holder comprising clamps 41, 42 at its ends, which on inserting the support into the holder are resiliently swung outwards, clamping the support 32 therein. Furthermore the clamps 41,42 may be formed with hooks 43,44, which grip into notched recesses 45, 46 on the sides of the support 32 and prevent the latter from being inadvertently detached from the holder 40.

I claim:

1. A container for receiving and supporting medical instruments, comprising:

a lower wire-formed part including first and second sides;

a lid removably connected to said lower part and including a first end, a second end, a top side, means on said lid first end for positively locking said first end of said lid to said first side of said lower part to removably and pivotally connect said lid first end and said lower part first side for pivotal movement of said lid and lower part about said pivotal connection and configured to define a biasing means for normally urging said lid second end away from and into spaced relation with said lower part second side, and a handle positioned on said top side;

latching means on one of said lid second end and said lower part second side for latching engagement and retention of said lid second end and said lower part second side when said lid second end is selectively displaced against said biasing means urgency into engagement with said lower part second side, said latching means being selectively operable for releasing said latched engagement of said lid second end and said lower part second side whereby said lid second side is urgently displaced by said biasing means into spaced relation with said lower part second side to thereby automatically open said container and provide access to medical instruments supported in and to be received in said container;

means for supporting medical instruments, said supporting means being removably positioned in said lower part and defining at least one receptacle for receiving a medical instrument; and means for bracing a medical instrument within the at least one receptacle, said lid being pivotally movable between a first closed position in which said lid second end is engaged with said lower part second side and said brace means acts to restrict access to the at least one receptacle, and a second open position in which said lid second end is separated and spaced from said lower part second side and the at least one receptacle is open and accessible to permit selective movement of a medical instrument into and out from the at least one receptacle.

2. The container of claim 1, wherein said lower part, a horizontal circumferential carrier extending around said lower part and a spring element positioned on said second side; said positive locking means includes projections for engaging said circumferential carrier; and said latching means includes a key for releasably engaging said spring element.

3. The container of claim 1, wherein said handle comprises first and second opposingly positioned U-shaped wires.

4. The container of claim 1, wherein said lower part has a width, and said support means includes first and second ends, said support means positioned to extend along the width of said lower part and being releasably connected to said lower part at said first and second ends.

5. The container of claim 1, wherein said lower part further includes first and second side walls each including a plurality of webs spaced therealong, and said support means is comprised of wire formed parts and further includes first and second ends and projections defining shoulders extending from each of said first and second ends, said support means being restrainably positioned within said lower part so that said projections extend between two of said plurality of webs on both said first and second side walls of said lower part and the shoulders are positioned against said two webs.

6. The container of claim 5, wherein said lid further includes first and second side walls each including a plurality of webs spaced therealong, and said brace means is comprised of wire-formed parts and includes first and second ends and projections defining shoulders extending from each of said first and second ends, said brace means being positioned within said lid so that said projections extend between two of said plurality of webs on both said first and second side walls of said lid and the shoulders are positioned against said two webs.

7. The container of claim 6, wherein said at least one receptacle is further defined by first and second parallelly extending U-shaped wire bends for accommodating the medical instruments and said brace means further includes means for restricting access to the at least one receptacle to fix instruments within said first and second U-shaped wire bends when said lid is in said closed position.

8. The container of claim 6, wherein both said brace means and support means further include a plastic coating.

9. The container of claim 1, wherein said support means is comprised of plastic and said at least one receptacle is further defined by first and second bendable flaps, the first and second bendable flaps positioned to allow access to the at least one receptacle when said lid is in said open position and positioned to restrict access to the at least one receptacle when said lid is in said closed position.

10. The container of claim 9, wherein said first and second flaps extend angularly and convergingly from said support means.

11. The container of claim 9, further comprising a holder positioned within said lower part, said holder including resiliently swinging clamping means for fixedly connecting said support means within said holder.

12. The container of claim 11, wherein said support means further includes first and second sides each defining a recess for receiving said clamping means.

13. The container of claim 12, wherein said clamping means includes first and second hooks each gripping the recess in a respective one of said first and second sides of said support means.

* * * * *